United States Patent [19]

Juan

[11] Patent Number: 4,809,370
[45] Date of Patent: Mar. 7, 1989

[54] APPARATUS FOR ASSISTING IN BOWEL EVACUATION

[76] Inventor: Chung W. Juan, 2150 N. McCord Rd., Suite F-103, Venetian Woods Condominium, Toledo, Ohio 43615

[21] Appl. No.: 214,937

[22] Filed: Jul. 5, 1988

[51] Int. Cl.$^4$ ................................................ A47K 3/00
[52] U.S. Cl. ...................................... 4/661; 4/420.3; 4/420.4; 4/446; 4/447
[58] Field of Search ............................. 4/420.1–420.5, 4/443–448, 661; 128/65, 66; 604/317, 322

[56] References Cited

U.S. PATENT DOCUMENTS

| | | | |
|---|---|---|---|
| 2,427,807 | 9/1947 | Oliver | 4/445 |
| 2,632,179 | 3/1953 | Trotter | 128/66 X |
| 3,288,140 | 11/1966 | McCarthy | 4/420.1 X |
| 3,577,567 | 5/1971 | Wintercorn | 4/420.1 X |
| 3,795,015 | 3/1974 | Talge et al. | 4/420.3 |
| 4,670,920 | 6/1987 | Juan | 4/661 |

FOREIGN PATENT DOCUMENTS

| | | | |
|---|---|---|---|
| 912432 | 8/1946 | France | 4/420.3 |
| 1387728 | 12/1964 | France | 4/420.3 |
| 465094 | 8/1951 | Italy | 4/420.3 |

*Primary Examiner*—Charles E. Phillips
*Attorney, Agent, or Firm*—Robert J. Black

[57] ABSTRACT

Apparatus for assisting in the evacuation of the waste matter (feces) present in the rectum and sigmoid colon consisting of a framelike structure supporting a container of warm water so positioned that the anus of the user is submersed in the water. Adapted for use on a flush toilet, connections are included to a source of warm water. Also included as a part of the water container are means for emptying the container into the associated toilet while the apparatus is in use.

9 Claims, 2 Drawing Sheets

APPARATUS FOR ASSISTING IN BOWEL EVACUATION

BACKGROUND OF THE INVENTION

1. Field of the Invention

The present invention relates to a method of assisting the defecation of mechanism in the ano-rectal region and promoting function of that mechanism and more particularly to apparatus for use in providing such assistance.

2. Background Art

One of the most common ailments of mankind has for centuries been recognized as constipation. The causes of unsuccessful evacuation or functional constipation frequently include such things as poor circulation in the ano-rectal region, weak ano-rectal muscles, intestinal gas, lack of coordination of the defecation mechanism of the ano-rectal region, hard feces and incomplete previous evacuation.

It has been determined that the immediate causes of functional constipation are closely related, inasmuch as the ano-rectal region is very rich in blood vessels, blood circulation in the particular region is a very important function. However, circulation may be restrained in this region by the presence of excessive waste matter in the sigmoid colon and rectum. Likewise, successful evacuation of waste matter out of the sigmoid colon and rectum is possible only when the ano-rectal muscles are in good physical condition. That is to say that they are healthy and strong enough to stand firm without flinching under the downward defecating force exerted by the defecation mechanism in the upper abdominal region so that force acts only on the waste matter in the sigmoid colon and rectum without loss, to result in successful evacuation. Unfortunately, ano-rectal muscles are often weakened and fatigued, blood circulation in the region is worsened by the overloaded straining stool, and the coordination of the defecation mechanism in ano-rectal region is then blocked causing the rectum and anal canal holding their waste matter contents to flinch as a whole rather than permitting their evacuation. The effect of the downward defecating force exerted by the defecation mechanism in the upper abdominal region is of little avail if it results in providing little relief to the individual suffering from constipation. Another problem frequently associated with constipation is the presence of gas in the intestines. While there is always some gas in the intestines, the gas is compressible, thus, the presence of gas in the intestines especially in the sigmoid colon and rectum is able to frustrate successful evacuation of the waste matter contained therein. A considerable amount of gas will be eliminated out of the sigmoid colon and rectum as a matter of course when the ano-rectal muscles are functioning properly and blood circulation in the area is satisfactory.

Without proper functioning of the defecation mechanism in the ano-rectal region, there is no successful evacuation going to occur. Thus only when the ano-rectal muscles are in any easy, comfortable, relaxed, sensitive and active state, are they alert enough to give prompt, full organic systematic coordination in the defecation process. Unfortunately, straining to eliminate the stools contained therein weakens and fatigues the ano-rectal muscles and dampens their sensitivity and coordination depressing or restraining blood circulation in the ano-rectal region.

Yet another case of functional constipation is the presence of hard feces. It is well recognized that hard waste matter is much more difficult to be eliminated than the soft. Similarly, incomplete previous evacuation is also a cause of constipation inasmuch as it frequently causes the waste matter that stays in the intestine when incomplete evacuation occurs to harden causing the difficulties in evacuation that occur with hard feces as noted above.

Many different techniques or compounds have been suggested and used in the past for relief of functional constipation. These include the use of laxatives, purges, enemas, suppositories, fibrous and filler diets, lubricants and even acupuncture. None of these techniques has been found to be completely successful in relieving the problems of functional constipation. Some techniques may be successful depending upon the cause behind the functional constipation, while other techniques have proved virtually useless in all cases. Representative of some of the diversed techniques employed that aid the constipation sufferer are those found in U.S. Pat. No. 1,525,505 to G. L. Kavanagh and U.S. Pat. No. 2,099,118 to G. W. Kennedy. Yet another technique is disclosed in my U.S. Pat. No. 4,670,920 which issued on June 9, 1987. Accordingly, it is the object of the present invention to provide a new and useful method of assisting in the evacuation of the waste matter (feces) present in the rectum and sigmoid colon and apparatus useful for providing or assisting in the provision of such technique.

SUMMARY OF THE INVENTION

The present invention consists basically of an adapter intended to be placed on a conventional toilet unit in place of the usual toilet seat. The adapter unit includes therein a bowl-like container in which a bath of warm water or similar aqueous solution is placed. The user then places him or herself in such a position that the anus is dipped into the liquid solution up to the end of the vertebrae (the coccyx bone) to effect defecation.

In the present embodiment, the bowl includes an opening against which a stopper is located. The stopper can be withdrawn from the opening to allow the contents of the bowl to be emptied into the toilet at any time by operating a handle which is connected by means of a shaft and associated tab to a flap associated with the stopper located at the rear of the adapter unit. Also included in the adapter unit is a warm water supply connection which is adapted for connection to an adjacent sink or other source of warm water with the water supply element of the adapter having an opening therein which allows the water to be sprayed out in such a manner that the running warm water showers the user's acupunctural meridians of defecation.

Use of the warm bath of the present invention provides a physical means that is unprecedented in its success for use in inducing the reflex action necessary to promote local blood circulation in the ano-rectal region and to assist in the tremendous effort required for successful evacuation. In the present invention the user places himself on the adapter unit in such a manner that the anus is dipped up to and above the coccyx bone in the warm water so that the weakened anal rectal muscles are immediately supported from below by the water substance and strengthened through the promoted blood circulation in the muscles. This warm water bath provides an ideal support so such weakened ano-rectal muscles since it does not stop the outlet opening of the anus.

As noted previously, the warm water bowl-like container provides an opening of approximately 4" in diameter which has a stopper which can be opened at any moment during evacuation to provide for emptying of the bowl. The running water can then refill the bowl all the time during evacuation and the warm water can be mainained in a clean condition. Adjacent to the bowl, channels are provided so that if the bowl becomes completely full, the overflow will empty directly into the toilet itself.

When the user sits on the adapter unit with the anus dipped into the bath of warm water and with the running warm water showering the user's acupunctural meridians of defecation, the user will find the sensitive ano-rectal muscles responding to the comforting ambience offered by the bath of warm water which revives the good coordination of the elements of the defecation mechanism in the ano-rectal region and which also improves the local blood circulation. It should also be noted that the water rises into the rectum between the wall of the rectum and any waste matter contained therein, thus serving as a lubricant and softener of dry and/or hard feces. This results in more easy evacuation.

DESCRIPTION OF THE PREFERRED EMBODIMENT

Figure 1:
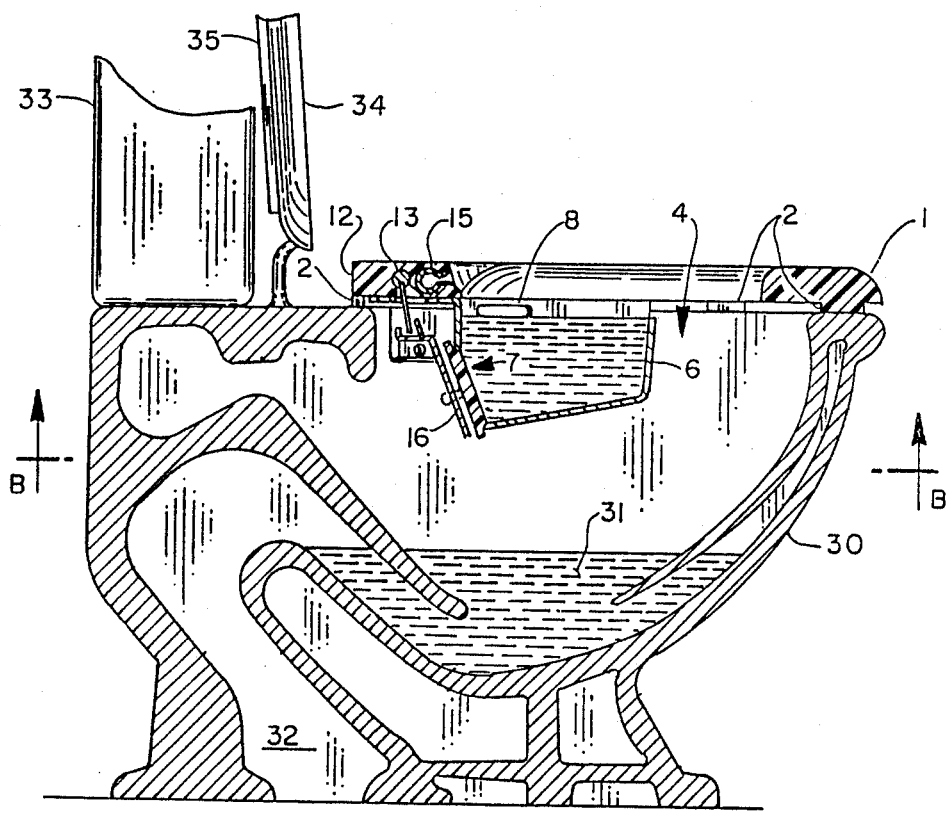
FIG. 1 is a cross-section of a conventional toilet taken along section lines AA of FIG. 2 and showing mounted thereon the adapter unit that constitutes the present invention.
Figure 2:
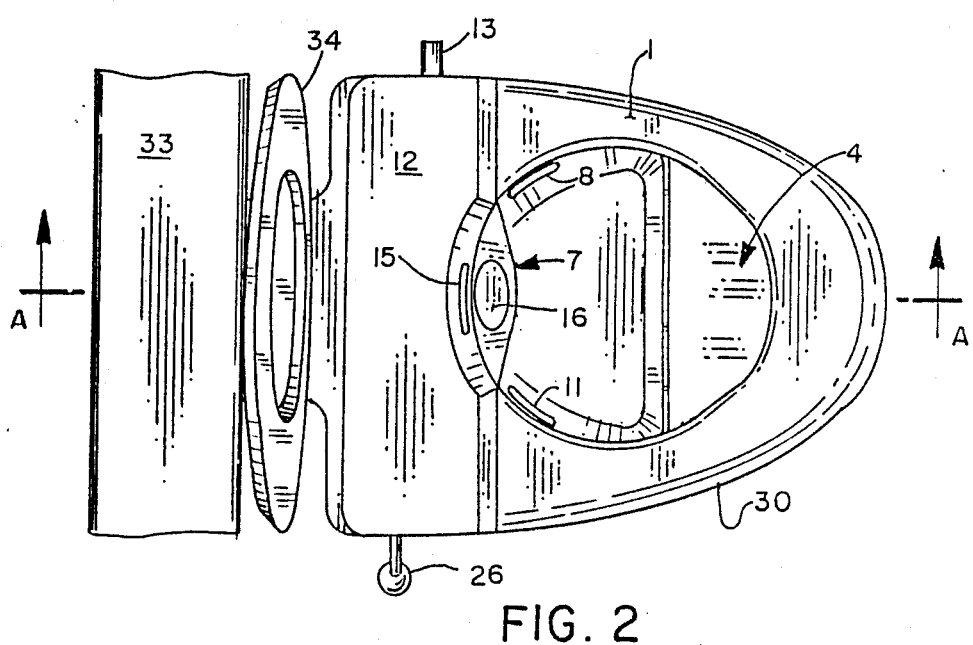
FIG. 2 is a top view of a toilet equipped with the adapter unit of the present invention.
Figure 3:
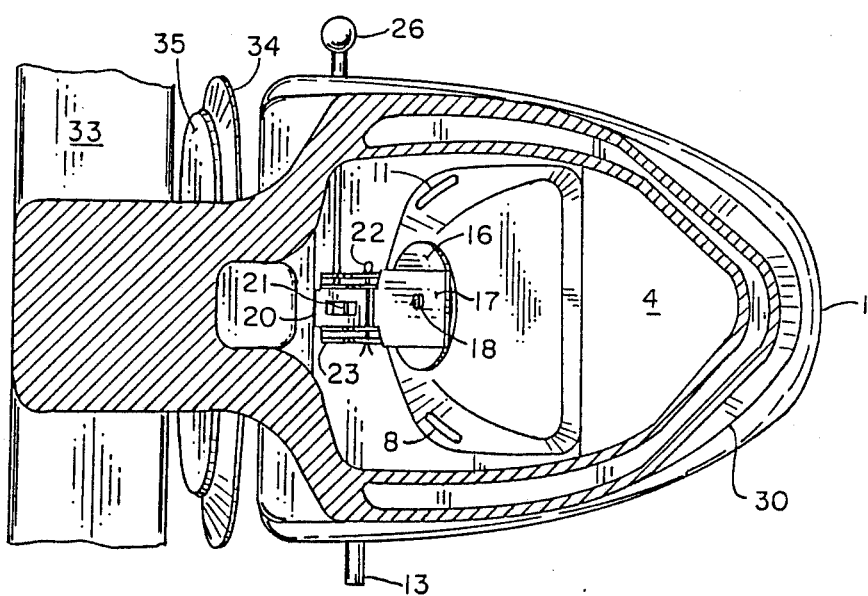
FIG. 3 is a cross-sectional view of a conventional toilet taken along section lines B—B of FIG. 1 and looking upward and showing an adapter unit in accordance with the present invention mounted thereon.

Referring now to FIGS. 1 and 2, the apparatus of the present invention which is designed to facilitate evacuation of the fecal matters in the rectum and sigmoid colon to overcome functional constipation and similar problems is shown mounted on a conventional toilet 30 containing water 31 therein, an outlet 32 for the toilet, watertank 33 with toilet seat 34 and an associated cover 35 shown in the upright or folded back position.

Located on the toilet is the adapter unit 1 which fits over the entire opening of a conventional toilet bowl supported on legs 2. Included in the adapter of the present invention is the bowl portion 6 which is open on top with the walls thereof all generally inclined inward in a downard direction. The bottom also slopes downward toward the rear of the bowl unit.

Included in the rear wall of the bowl unit is an opening 7 of approximately 4" in diameter. This bowl opening is normally blocked by a stopper element 16 which provides a waterproof seal to the bowl unit opening 7.

Figure 4A:
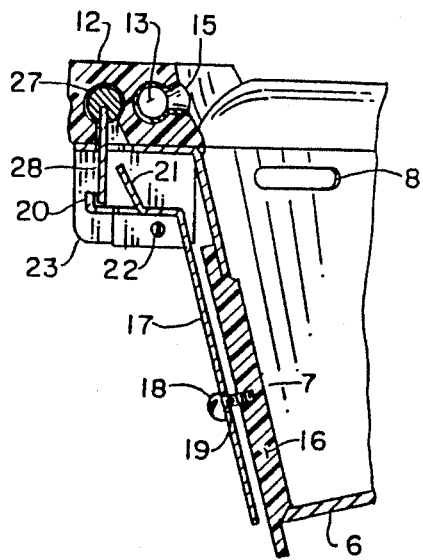
FIG. 4A is an enlarged partial cross-sectional view of a toilet as shown in FIG. 3, showing the stopper mechanism of the present invention in the closed position.
Figure 4B:
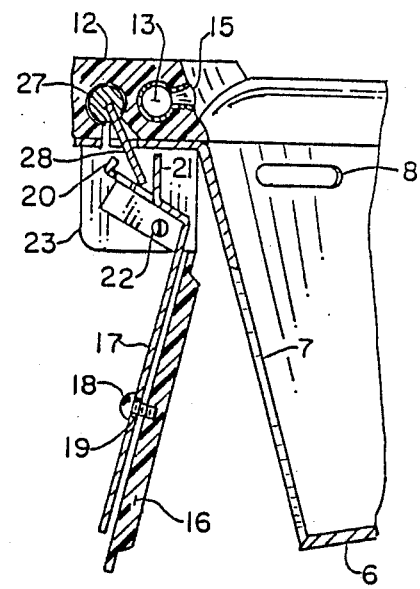
FIG. 4B is an enlarged partial cross-sectional view of a toilet as shown in FIG. 3, showing the stopper mechanism of the present invention in the open position.
Figure 5:
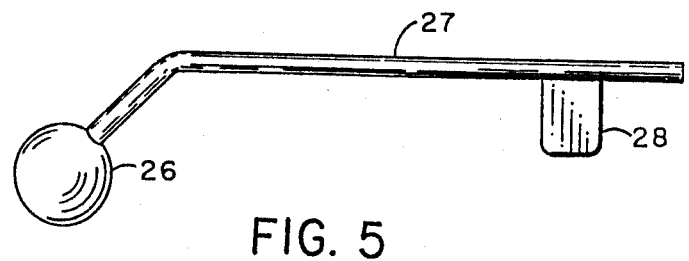
FIG. 5 is a side view of the operating handle, shaft and tab associated with the stopper mechanism of the present invention.

As may be seen in FIG. 1 and more clearly in FIGS. 4A and 4B, the stopper element 16 which may be made of rubber or certain flexible plastics is so contoured as to nest on a water tight basis into opening 7 of bowl unit 6. Stopper element 16 is affixed to plunger support 17 and held in place therein by means of screw or similar fastening means 18. The support mechanism 17 further includes a trigger mechanism section 20 extending angularly away from the basic support mechanism 17 with the trigger mechanism 20 further including a raised projecting flap 21. The plunger support 17 and the trigger mechanism 20, with its included flap 21 is supported from the adapter unit of the present invention by means of a U-shaped saddle bracket 23 and arranged to pivot about a point 22 where it is supported by a cotter pin or spring pin to the saddle bracket.

In the normal or closed position, with the stopper 16 engaging the opening 7, tab 28 presses in a downward direction against trigger mechanism retaining the plunger support 17 and plunger 16 in the closed position. In response to operation by the user, the handle 26 is grasped and rotated in a forward direction causing shaft 27 to rotate in a counter-clockwise direction as viewed in FIGS. 4A and 4B which in turn causes tab 28 to move in a forward direction against flap 21. This action then urges the entire mechanism consisting of trigger mechanism 20 and plunger support 17 and associated plunger 16, in a direction to rotate about pivot point 22 whereby the plunger 16 is withdrawn from opening 7 allowing the contents of bowl 6 to be deposited into the main portion of toilet 30.

The user may then return handle 26 to its normal position causing shaft 27 to rotate in a clockwise direction as seen in FIGS. 4A and 4B whereby tab 28 will disengage from flap 21 and at the same time will move backward against trigger mechanism 20 forcing the entire assembly to rotate about pivot point 22 and urging stopper 16 back into position to close opening 7 in bowl 6.

Also included in the adapter unit of the present invention is a half-moon-shaped opening 4 to accommodate the genitals for passing urine directly into the bowl of the toilet to keep the warm water from becoming roiled.

It should be further noted that the bowl portion 6 of the present invention is of such construction that the opening tapers from the front wall to the back with the largest distance from the right to left in the present embodiment being approximately 10" and that from front to back being about 8". In the embodiment of the present invention it is shown that there is no clear division between the bottom and two lateral side walls, the bottom being a continuation of the lateral walls and vice versa. The two lateral side walls extend downward and incline inward gradually approaching, and meet each other to form the bottom. This bottom portion then tapers and slopes downward from the front wall to meet the back wall to facilitate emptying the bowl through the opening 7 contained in the rear wall as discussed previously. It should then be noted that there is a recess 5 in the whole top of the front wall of the bowl 6 as a continuation of the half-moon-shaped opening 4 in the front portion of the adapter unit forming the urination passage.

As may be seen by reference to FIG. 2, the adapter unit is equipped with two spillways designated 8 and 9 for overflow of water from bowl 6, one on each lateral wall adjacent to the back wall of the bowl 6. The recess in the whole top of front wall of bowl 6 and spillways 8 and 9 are on the same level.

A particular feature of the present invention is the inclusion of a running warm water supply system contained within block 12 as seen in FIG. 2 as well as shown in cross section in FIG. 1. Included therein as may be seen in FIG. 1 is a channel which extends from an opening 13 located on one side of the adapter unit to outlet 15. An additional connection may be provided to the channel at a location on its underside and opening 13 is then plugged. As may be seen in FIG. 2, outlet 15 extends from the channel extending from opening 13. This opening is slit-like in appearance and about ¾" in breadth and is connected to the warm water supply channel. Alternately, a line of a series of small holes ⅛" in diameter could be employed. In usage, the opening 13 can be used as an inlet for warm water connected from a faucet (or other source of water usually available in or adjacent to a bathroom) by means of conventional state-of-the-art adapters and a connecting tube or hose.

The adapter unit of the present invention is a portable device as noted previously to encourage and faciliate successful bowel evacuation. When in use, it is placed on an ordinary toilet bowl 30 with inlet 13, of the water supply being connected to a faucet supplying warm water by means of an adapter with connected tubing. The warm water is then caused to exit through warm water opening 15 which is used to shower the acupunctural meridian of defecation of the user as well as to fill the bowl 6 which is utilized as a warm water bath to assist in successful bowel evacuation. It has been determined that water temperatures in the nature of 100 degrees F. to 122 degrees F. are most generally beneficial for this purpose. Generally speaking, the higher the temperature of the warm water bath within the specified range, the better its effect in strengthening the defecation mechanism and promoting its function. However, each user should choose his or her own optimum temperature within the above range of specified temperatures.

As noted previously, theuser of the adapter unit of the present invention sits on the bowl 6 with the anus immersed in the warm water with the outlet 15 aimed at the region above the coccyx of the user as a supplementary means to assist in bowel evacuation. After defecation, waste matter evacuated into the warm water bath in the bowl, is then emptied into the toilet bowl at any desired time. This is accomplished by pulling the handle 26 in a forward direction. After emptying the bowl 6, the opening 7 will be closed by the stopper 16 in response to returning the handle to the normal position. As noted previously, an opening 4 is provided to facilitate the direct passage of urine into the toilet bowl. If urine were to be passed into the warm water bath bowl 6, the stream of urine might also disturb stools already evacuated into the bowl causing them to disburse into pieces and become suspended into the bath of diluted urine. Thus the clean clear warm water bath in the bowl would become an infectious medium, a bath of urine and fecal mud which would constitute a serious menace to the urogenital organs and also to successful evacuation.

It will be seen from the foregoing that the present invention consists of a comfortable seat for placement on a conventional toilet unit which includes a warm water bath bowl allowing the user to be able to immerse the anus in warm water up to and above the coccyx bone, at the same time excluding the genitals out of the bowl area. This is done so that urine may be passed directly into the toilet, rather than into the same warm water bath bowl as wast matter evacuated from the bowel. Of prime importance also is the inclusion of an easy closing system used for emptying of the bowl to maintain a clean warm water bath portion to assist in the defecation process.

Attached to the rear portion of the present invention is a descending bumper portion 14 placed in proximity to the rear portion of the opening of the toilet 30. This bumper 14 acts to prevent the entire assembly from sliding too far back, thus assisting in maintaining the proper positioning of the apparatus on the supporting toilet structure.

While but a single embodiment of the present invention has been shown, it will be obvious to those skilled in the art that numerous modifications can be made without departing from the spirit of the present invention which shall be limited only by the scope of the claims appended hereto.

What is claimed is:

1. Means for assisting in the evacuation of the rectum and sigmoid colon, including support means and adapter means positioned on said support means, said adapter means comprising:

a seat portion adapted to support a user in a seated position on said seat portion;

an opening through said adapter to facilitate urination by said user;

an open top container adapted to contain therein warm water, said container substantially bowl shaped and positioned so the anus of the user can be positioned in said water up to the coccyx;

a water distribution means comprising a tube-like structure open at one end thereof and including at least one aperature located at the other end of said tube-like structure;

said water distribution means adapted to be connected to a source of warm water and said aperture so positioned that water from said source is projected against the acupunctural meridians of defecation of the user;

said open top container further containing a discharge opening to facilitate the discharge of the contents of said container into said support means and support means positioned to normally maintain said opening closed;

and means for removing said stopper from said opening, including a handle projeced external of said seat portion, connected to a shaft including a tab; said tab engaging a trigger mechanism associated with said stopper, operated in response to the manual movement of said handle to withdraw said stopper means from said discharge opening.

2. Means for assisting in the evacuation of the rectum and sigmoid colon as claimed in claim 1 wherein:

said trigger mechanism further includes an upward projecting flap adapted to engage said tab and in response to operation of said handle to become engaged with said flap and thereby to force a support mechanism associated with said stopper in a direction away from said opening to withdraw said stopper from said opening to facilitate the discharge of the contents of said bowl into said support means.

3. Means for assisting in the evacuation of the rectum and sigmoid colon as claimed in claim 2 wherein:

said stopper is attached to said support mechanism.

4. Means for assisting in the evacuation of the rectum and sigmoid colon as claimed in claim 3 wherein:
said trigger mechanism and said support mechanism are joined each to the other and adapted to be supported from said support means by a saddle bracket and allowed to move about a pivot point in a rotational direction away from said opening or in the alternative towards said opening.

5. Means for assisting in the evacuation of the rectum and sigmoid colon as claimed in claim 1 wherein:
said tube-like structure at said open end is adapted to be connected to a source of warm water.

6. Means for assisting in the evacuation of the rectum and sigmoid colon as claimed in claim 1 wherein:
said adapter means further includes overflow means located adjacent to said open top container providing a path for an excess of warm water in said open top container to be channeled to said support means.

7. Means for assisting in the evacuation of the rectum and sigmoid colon as claimed in claim 6 wherein:
said overflow means comprise a plurality of overflow spillways positioned adjacent to said open top container and directed toward said support means.

8. Means for assisting in the evacuation of the rectum and sigmoid colon as claimed in claim 1 wherein:
said support means comprise a flush toilet.

9. Means for assisting in the evacuation of the rectum and sigmoid colon as claimed in claim 1 wherein:
said seat portion further includes a bumper adapted to be placed against a portion of said support means.

* * * * *